(12) United States Patent
Thompson

(10) Patent No.: US 11,781,154 B2
(45) Date of Patent: Oct. 10, 2023

(54) COMPOSITIONS AND METHODS FOR REGULATING PRODUCTION OF A FUSION PROTEIN AND RIBONUCLEIC ACID

(71) Applicant: Wyvern Pharmaceuticals Inc., Calgary (CA)

(72) Inventor: Bradley G Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 260 days.

(21) Appl. No.: 17/076,721

(22) Filed: Oct. 21, 2020

(65) Prior Publication Data
US 2022/0119838 A1    Apr. 21, 2022

(51) Int. Cl.
| | |
|---|---|
| *C12N 15/79* | (2006.01) |
| *C07H 21/04* | (2006.01) |
| *C12N 15/86* | (2006.01) |
| *C07K 14/705* | (2006.01) |
| *C12N 15/113* | (2010.01) |
| *C12N 7/00* | (2006.01) |

(52) U.S. Cl.
CPC ........ *C12N 15/86* (2013.01); *C07K 14/70521* (2013.01); *C12N 7/00* (2013.01); *C12N 15/1136* (2013.01); *C07K 2319/31* (2013.01); *C07K 2319/33* (2013.01); *C12N 2310/14* (2013.01); *C12N 2320/31* (2013.01); *C12N 2320/32* (2013.01); *C12N 2750/14143* (2013.01); *C12N 2750/14171* (2013.01)

(58) Field of Classification Search
CPC ................ C12N 15/86; C12N 2310/14; C12N 2750/14143; C07H 21/02; C07H 21/04
See application file for complete search history.

*Primary Examiner* — Shin Lin Chen
(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for increasing production of a belatacept-similar protein and interfering RNA of tumor necrosis factor alpha. Embodiments of the present disclosure can be used as a therapy or a treatment for a subject that has a condition whereby the subject's immune system is, or is likely to become, dysregulated and where the production of the belatacept-similar protein and decreased production of tumor necrosis factor alpha may be of therapeutic benefit.

10 Claims, 5 Drawing Sheets

Specification includes a Sequence Listing.

FIG. 1

FIG. 3

SEQUENCE LISTING

<160> NUMBER OF SEQ ID NOS: 17

<210> SEQ ID NO 1
<211> LENGTH: 375
<212> TYPE: DNA
<213> ORGANISM: Artificial Sequence
<220> FEATURE:
<223> OTHER INFORMATION: Synthetic Sequence [Belatacept]

<400> SEQUENCE: 1

```
atgcacgtgg cccagcctgc tgtggtactg gccagcagcc gaggcatcgc cagctttgtg      60
tgtgagtatg catctccagg caaatacact gaggtccggg tgacagtgct tcggcaggct     120
gacagccagg tgactgaagt ctgtgcggca acctacatga tggggaatga gttgaccttc     180
ctagatgatt ccatctgcac gggcacctcc agtggaaatc aagtgaacct cactatccaa     240
ggactgaggg ccatggacac gggactctac atctgcaagg tggagctcat gtacccaccg     300
ccatactacg agggcatagg caacggaacc cagatttatg taattgatcc agaaccgtgc     360
ccagattctg atcag                                                     375
```

<210> SEQ ID NO 2
<211> LENGTH: 155
<212> TYPE: DNA
<213> ORGANISM: Artificial Sequence
<220> FEATURE:
<223> OTHER INFORMATION: Synthetic Sequence [miR-E1 Cassette]

<400> SEQUENCE: 2

```
cgacttctta acccaacaga aggctcgaga aggtatattg ctgttgacag tgagcgcgct      60
atctcatacc aggagaaaata gtgaagccac agatgtatt ctcctggtat gagatagcat     120
gcctactgcc tcggacttca aggggctaga attcg                                155
```

<210> SEQ ID NO 3
<211> LENGTH: 155
<212> TYPE: DNA
<213> ORGANISM: Artificial Sequence
<220> FEATURE:
<223> OTHER INFORMATION: Synthetic Sequence [miR-E2 Cassette]

<400> SEQUENCE: 3

```
cgacttctta acccaacaga aggctcgaga aggtatattg ctgttgacag tgagcgacaa      60
accaccaagt ggaggagcta gtgaagccac agatgtagct cctccacttg gtggtttgct     120
gcctactgcc tcggacttca aggggctaga attcg                                155
```

<210> SEQ ID NO 4
<211> LENGTH: 155
<212> TYPE: DNA
<213> ORGANISM: Artificial Sequence
<220> FEATURE:
<223> OTHER INFORMATION: Synthetic Sequence [miR-E3 Cassette]

<400> SEQUENCE: 4

```
cgacttctta acccaacaga aggctcgaga aggtatattg ctgttgacag tgagcgacca      60
agtacttaga ctttgcggta gtgaagccac agatgtaccg caaagtctaa gtacttgggt     120
gcctactgcc tcggacttca aggggctaga attcg                                155
```

<210> SEQ ID NO 5
<211> LENGTH: 465
<212> TYPE: DNA
<213> ORGANISM: Artificial Seqeunce
<220> FEATURE:
<223> OTHER INFORMATION: Synthetic Sequence [miR-E1, -E2 and -E3 Cassettes]

<400> SEQUENCE: 5

```
cgacttctta acccaacaga aggctcgaga aggtatattg ctgttgacag tgagcgcgct      60
atctcatacc aggagaaata gtgaagccac agatgtattt ctcctggtat gagatagcat     120
gcctactgcc tcggacttca aggggctaga attcgcgact tcttaaccca acagaaggct     180
cgagaaggta tattgctgtt gacagtgagc gacaaaccac caagtggagg agctagtgaa     240
gccacagatg tagctcctcc acttggtggt ttgctgccta ctgcctcgga cttcaagggg     300
ctagaattcg cgacttctta acccaacaga aggctcgaga aggtatattg ctgttgacag     360
tgagcgacca agtacttaga ctttgcggta gtgaagccac agatgtaccg caaagtctaa     420
gtacttgggt gcctactgcc tcggacttca aggggctaga attcg                     465
```

<210> SEQ ID NO 6
<211> LENGTH: 1679
<212> TYPE: DNA
<213> ORGANISM: Artificial Sequence
<220> FEATURE:
<223> OTHER INFORMATION: Synthetic Sequence [Entire Insert]

<400> SEQUENCE: 6

```
ggtaccgcca ccatggccac cggctctcgc acaagcctgc tgctggcttt cggactgctg      60
tgcctgcctt ggctccagga gggctccgcc atgcacgtgg cccagcctgc tgtggtactg     120
gccagcagcc gaggcatcgc cagctttgtg tgtgagtatg catctccagg caaatacact     180
gaggtccggg tgacagtgct tcggcaggct gacagccagg tgactgaagt ctgtgcggca     240
acctacatga tggggaatga gttgaccttc ctagatgatt ccatctgcac gggcacctcc     300
agtggaaatc aagtgaacct cactatccaa ggactgaggg ccatggacac gggactctac     360
atctgcaagg tggagctcat gtacccaccg ccatactacg agggcatagg caacggaacc     420
cagatttatg taattgatcc agaaccgtgc ccagattctg atcagggatc cggaggagga     480
ggcagcggag gaggcggatc tggcggaggc ggaagcgaca agacccacac atgcccacca     540
tgtcctgcac ctgaactcct ggggggaccg tcagtcttcc tcttcccccc aaaacccaag     600
gacaccctca tgatctcccg gacccctgag gtcacatgcg tggtggtgga cgtgagccac     660
gaagaccctg aggtcaagtt caactggtac gtggacggcg tggaggtgca taatgccaag     720
acaaagccgc gggaggagca gtacaacagc acgtaccgtg tggtcagcgt cctcaccgtc     780
ctgcaccagg actggctgaa tggcaaggag tacaagtgca aggtctccaa caaagccctc     840
ccagccccca tcgagaaaac catctccaaa gccaaagggc agccccgaga accacaggtg     900
tacaccctgc cccatcccgg gaggagatg accaagaacc aggtcagcct gacctgcctg     960
gtcaaaggct tctatcccag cgacatcgcc gtggagtggg agagcaatgg gcagccggag    1020
aacaactaca agaccacgcc tcccgtgctg gactccgacg gctccttctt cctctacagc    1080
aagctcaccg tggacaagag caggtggcag caggggaacg tcttctcatg ctccgtgatg    1140
catgaggctc tgcacaacca ctacacgcag aagagcctct ccctgtctcc gggtaaatag    1200
cgctagccga cttcttaacc caacagaagg ctcgagaagg tatattgctg ttgacagtga    1260
gcgcgctatc tcataccagg agaaatagtg aagccacaga tgtatttctc tggtatgag    1320
atagcatgcc tactgcctcg gacttcaagg ggctagaatt cgcgacttct taacccaaca    1380
gaaggctcga gaaggtatat tgctgttgac agtgagcgac aaaccaccaa gtggaggagc    1440
```

| | | |
|---|---|---|
| tagtgaagcc acagatgtag ctcctccact tggtggtttg ctgcctactg cctcggactt | 1500 | |
| caaggggcta gaattcgcga cttcttaacc caacagaagg ctcgagaagg tatattgctg | 1560 | |
| ttgacagtga gcgaccaagt acttagactt tgcggtagtg aagccacaga tgtaccgcaa | 1620 | |
| agtctaagta cttgggtgcc tactgcctcg gacttcaagg ggctagaatt cgtctagaa | 1679 | |

```
<210> SEQ ID NO 7
<211> LENGTH: 7520
<212> TYPE: DNA
<213> ORGANISM: Artificial Sequence
<220> FEATURE:
<223> OTHER INFORMATION: Synthetic Sequence  [Whole Vector]

<400> SEQUENCE: 7
```

| | | |
|---|---|---|
| cagcagctgc gcgctcgctc gctcactgag gccgcccggg caaagcccgg gcgtcgggcg | 60 | |
| acctttggtc gcccggcctc agtgagcgag cgagcgcgca gagagggagt ggccaactcc | 120 | |
| atcactaggg gttccttgta gttaatgatt aacccgccat gctacttatc tacgtagcca | 180 | |
| tgctctagga cattgattat tgactagtgg agttccgcgt tacataactt acggtaaatg | 240 | |
| gcccgcctgg ctgaccgccc aacgacccc gcccattgac gtcaataatg acgtatgttc | 300 | |
| ccatagtaac gccaataggg actttccatt gacgtcaatg ggtggagtat ttacggtaaa | 360 | |
| ctgcccactt ggcagtacat caagtgtatc atatgccaag tacgcccct attgacgtca | 420 | |
| atgacggtaa atggcccgcc tggcattatg cccagtacat gaccttatgg gactttccta | 480 | |
| cttggcagta catctacgta ttagtcatcg ctattaccat ggtcgaggtg agccccacgt | 540 | |
| tctgcttcac tctccccatc tccccccct ccccaccccc aattttgtat ttatttattt | 600 | |
| tttaattatt ttgtgcagcg atggggcg gggggggg gggcgcgcg caggcggggc | 660 | |
| ggggcgggc gagggcggg gcgggcgag gcggagaggt gcggcggcag ccaatcagag | 720 | |
| cggcgcgctc cgaaagtttc cttttatggc gaggcggcgg cggcggcggc cctataaaaa | 780 | |
| gcgaagcgcg cggcgggcgg gagtcgctgc gcgctgcctt cgccccgtgc cccgctccgc | 840 | |
| cgccgcctcg cgccgcccgc cccggctctg actgaccgcg ttactaaaac aggtaagtcc | 900 | |
| ggcctccgcg ccgggttttg gcgcctcccg cgggcgcccc cctcctcacg gcgagcgctg | 960 | |
| ccacgtcaga cgaagggcgc agcgagcgtc ctgatccttc cgcccggacg ctcaggacag | 1020 | |
| cggcccgctg ctcataagac tcggccttag aaccccagta tcagcagaag gacattttag | 1080 | |
| gacgggactt gggtgactct agggcactgg ttttctttcc agagagcgga acaggcgagg | 1140 | |
| aaaagtagtc ccttctcggc gattctgcgg agggatctcc gtgggcggt gaacgccgat | 1200 | |
| gatgcctcta ctaaccatgt tcatgttttc tttttttttc tacaggtcct gggtgacgaa | 1260 | |
| cagggtaccg ccaccatggc caccggctct cgcacaagcc tgctgctggc tttcggactg | 1320 | |
| ctgtgcctgc cttggctcca ggagggctcc gccatgcacg tggcccagcc tgctgtggta | 1380 | |
| ctggccagca gccgaggcat cgccagcttt gtgtgtgagt atgcatctcc aggcaaatac | 1440 | |
| actgaggtcc gggtgacagt gcttcggcag gctgacagcc aggtgactga agtctgtgcg | 1500 | |
| gcaacctaca tgatggggaa tgagttgacc ttcctagatg attccatctg cacgggcacc | 1560 | |
| tccagtggaa atcaagtgaa cctcactatc caaggactga gggccatgga cacgggactc | 1620 | |
| tacatctgca aggtggagct catgtaccca ccgccatact acgagggcat aggcaacgga | 1680 | |
| acccagattt atgtaattga tccagaaccg tgcccagatt ctgatcaggg atccggagga | 1740 | |
| ggaggcagcg gaggaggcgg atctggcgga ggcggaagcg acaagaccca cacatgccca | 1800 | |

-continued

```
ccatgtcctg cacctgaact cctgggggga ccgtcagtct tcctcttccc cccaaaaccc    1860
aaggacaccc tcatgatctc ccggacccct gaggtcacat gcgtggtggt ggacgtgagc    1920
cacgaagacc ctgaggtcaa gttcaactgg tacgtggacg gcgtggaggt gcataatgcc    1980
aagacaaagc cgcggggagga gcagtacaac agcacgtacc gtgtggtcag cgtcctcacc    2040
gtcctgcacc aggactggct gaatggcaag gagtacaagt gcaaggtctc caacaaagcc    2100
ctcccagccc ccatcgagaa aaccatctcc aaagccaaag gcagccccg agaaccacag    2160 gtgtacaccc tgcccccatc ccgggaggag atgaccaaga accaggtcag cctgacctgc    2220
ctggtcaaag gcttctatcc cagcgacatc gccgtggagt gggagagcaa tgggcagccg    2280
gagaacaact acaagaccac gcctcccgtg ctggactccg acggctcctt cttcctctac    2340
agcaagctca ccgtggacaa gagcaggtgg cagcagggga acgtcttctc atgctccgtg    2400
atgcatgagg ctctgcacaa ccactacacg cagaagagcc tctccctgtc tccgggtaaa    2460
tagcgctagc cgacttctta acccaacaga aggctcgaga aggtatattg ctgttgacag    2520
tgagcgcgct atctcatacc aggagaaata gtgaagccac agatgtattt ctcctggtat    2580
gagatagcat gcctactgcc tcggacttca aggggctaga attcgcgact tcttaaccca    2640
acagaaggct cgaaaggta tattgctgtt gacagtgagc gacaaaccac caagtggagg    2700
agctagtgaa gccacagatg tagctcctcc acttggtggt ttgctgccta ctgcctcgga    2760
cttcaagggg ctagaattcg cgacttctta acccaacaga aggctcgaga aggtatattg    2820
ctgttgacag tgagcgacca agtacttaga cttttgcggta gtgaagccac agatgtaccg    2880
caaagtctaa gtacttgggt gcctactgcc tcggacttca aggggctaga attcgtctag    2940
aataatcaac ctctggatta caaaatttgt gaaagattga ctggtattct taactatgtt    3000 gctccttta cgctatgtgg atacgctgct ttaatgcctt tgtatcatgc tattgcttcc    3060
cgtatggctt tcattttctc ctccttgtat aaatcctggt tgctgtctct ttatgaggag    3120
ttgtggcccg ttgtcaggca acgtggcgtg gtgtgcactg tgtttgctga cgcaaccccc    3180
actggttggg gcattgccac cacctgtcag ctcctttccg ggactttcgc tttccccctc    3240
cctattgcca cggcggaact catcgccgcc tgccttgccc gctgctggac agggggctcgg    3300 ctgttgggca ctgacaattc cgtggtgttg tcggggaaat catcgtcctt tccttggctg    3360
ctcgcctgtg ttgccacctg gattctgcgc gggacgtcct tctgctacgt cccttcggcc    3420
ctcaatccag cggaccttcc ttcccgcggc ctgctgccgg ctctgcggcc tcttccgcgt    3480
cttcgccttc gccctcagac gagtcggatc tcccttggg ccgcctcccc gcctaagctt    3540
atcgataccg tcgagatcta acttgtttat tgcagcttat aatggttaca ataaagcaa    3600 tagcatcaca aatttcacaa ataaagcatt ttttcactg cattctagtt gtggtttgtc    3660
caaactcatc aatgtatctt atcatgtctg gatctcgacc tcgactagag catggctacg    3720
tagataagta gcatggcggg ttaatcatta actacaagga accctagtg atggagttgg    3780 ccactccctc tctgcgcgct cgctcgctca ctgaggccgg cgaccaaag tcgcccgac    3840 gcccgggctt tgcccgggcg gcctcagtga gcgagcgagc gcgccagctg gcgtaatagc    3900
gaagaggccc gcaccgatcg cccttcccaa cagttgcgca gcctgaatgg cgaatggaat    3960
tccagacgat tgagcgtcaa aatgtaggta tttccatgag cgttttcct gttgcaatgg    4020 ctggcggtaa tattgttctg gatattacca gcaaggccga tagtttgagt tcttctactc    4080
aggcaagtga tgttattact aatcaaagaa gtattgcgac aacggttaat ttgcgtgatg    4140
gacagactct tttactcggt ggcctcactg attataaaaa cacttctcag gattctggcg    4200
```

```
taccgttcct gtctaaaatc cctttaatcg gcctcctgtt tagctcccgc tctgattcta    4260
acgaggaaag cacgttatac gtgctcgtca aagcaaccat agtacgcgcc ctgtagcggc    4320
gcattaagcg cggcgggtgt ggtggttacg cgcagcgtga ccgctacact tgccagcgcc    4380
ctagcgcccg ctcctttcgc tttcttccct tcctttctcg ccacgttcgc cggctttccc    4440
cgtcaagctc taaatcgggg gctcccttta gggttccgat ttagtgcttt acggcacctc    4500
gaccccaaaa aacttgatta gggtgatggt tcacgtagtg ggccatcgcc ctgatagacg    4560
gtttttcgcc ctttgacgtt ggagtccacg ttctttaata gtggactctt gttccaaact    4620
ggaacaacac tcaaccctat ctcggtctat tcttttgatt tataagggat tttgccgatt    4680
tcggcctatt ggttaaaaaa tgagctgatt aacaaaaat ttaacgcgaa ttttaacaaa     4740
atattaacgt ttacaattta aatatttgct tatacaatct tcctgttttt ggggcttttc    4800
tgattatcaa ccgggtaca tatgattgac atgctagttt tacgattacc gttcatcgat     4860
tctcttgttt gctccagact ctcaggcaat gacctgatag cctttgtaga gacctctcaa    4920
aaatagctac cctctccggc atgaatttat cagctagaac ggttgaatat catattgatg    4980
gtgatttgac tgtctccggc ctttctcacc cgtttgaatc tttacctaca cattactcag    5040
gcattgcatt taaaatatat gagggttcta aaaattttta tccttgcgtt gaaataaagg    5100
cttctcccgc aaaagtatta cagggtcata atgtttttgg tacaaccgat ttagctttat    5160
gctctgaggc tttattgctt aattttgcta attctttgcc ttgcctgtat gatttattgg    5220
atgttggaat tcctgatgcg gtattttctc cttacgcatc tgtgcggtat ttcacaccgc    5280
atatggtgca ctctcagtac aatctgctct gatgccgcat agttaagcca gccccgacac    5340
ccgccaacac ccgctgacgc gccctgacgg gcttgtctgc tcccggcatc cgcttacaga    5400
caagctgtga ccgtctccgg gagctgcatg tgtcagaggt tttcaccgtc atcaccgaaa    5460
cgcgcgagac gaaagggcct cgtgatacgc ctatttttat aggttaatgt catgataata    5520
atggtttctt agacgtcagg tggcactttt cggggaaatg tgcgcggaac ccctatttgt    5580
ttatttttct aaatacattc aaatatgtat ccgctcatga caataaccc tgataaatg      5640 cttcaataat attgaaaaag gaagagtatg agtattcaac atttccgtgt cgcccttatt    5700 ccctttttg cggcattttg ccttcctgtt tttgctcacc cagaaacgct ggtgaaagta     5760
aaagatgctg aagatcagtt gggtgcacga gtgggttaca tcgaactgga tctcaacagc    5820
ggtaagatcc ttgagagttt tcgccccgaa gaacgttttc caatgatgag cacttttaaa    5880
gttctgctat gtggcgcggt attatcccgt attgacgccg ggcaagagca actcggtcgc    5940
cgcatacact attctcagaa tgacttggtt gagtactcac cagtcacaga aaagcatctt    6000
acggatggca tgacagtaag agaattatgc agtgctgcca taaccatgag tgataacact    6060
gcggccaact tacttctgac aacgatcgga ggaccgaagg agctaaccgc ttttttgcac    6120
aacatggggg atcatgtaac tcgccttgat cgttgggaac cggagctgaa tgaagccata    6180
ccaaacgacg agcgtgacac cacgatgcct gtagcaatgg caacaacgtt gcgcaaacta    6240
ttaactggcg aactacttac tctagcttcc cggcaacaat taatagactg gatggaggcg    6300
gataaagttg caggaccact tctgcgctcg gcccttccgg ctggctggtt tattgctgat    6360
aaatctggag ccggtgagcg tgggtctcgc ggtatcattg cagcactggg gccagatggt    6420
aagccctccc gtatcgtagt tatctacacg acggggagtc aggcaactat ggatgaacga    6480
aatagacaga tcgctgagat aggtgcctca ctgattaagc attggtaact gtcagaccaa    6540
```

-continued

```
gtttactcat atatacttta gattgattta aaacttcatt tttaatttaa aaggatctag    6600
gtgaagatcc tttttgataa tctcatgacc aaaatccctt aacgtgagtt ttcgttccac    6660
tgagcgtcag accccgtaga aaagatcaaa ggatcttctt gagatccttt ttttctgcgc    6720
gtaatctgct gcttgcaaac aaaaaaacca ccgctaccag cggtggtttg tttgccggat    6780
caagagctac caactctttt tccgaaggta actggcttca gcagagcgca gataccaaat    6840
actgtccttc tagtgtagcc gtagttaggc caccacttca agaactctgt agcaccgcct    6900
acatacctcg ctctgctaat cctgttacca gtggctgctg ccagtggcga taagtcgtgt    6960
cttaccgggt tggactcaag acgatagtta ccggataagg cgcagcggtc gggctgaacg    7020
gggggttcgt gcacacagcc cagcttggag cgaacgacct acaccgaact gagataccta    7080
cagcgtgagc tatgagaaag cgccacgctt cccgaaggga gaaaggcgga caggtatccg    7140
gtaagcggca gggtcggaac aggagagcgc acgagggagc ttccaggggg aaacgcctgg    7200
tatctttata gtcctgtcgg gtttcgccac ctctgacttg agcgtcgatt tttgtgatgc    7260
tcgtcagggg gcggagcct atggaaaaac gccagcaacg cggccttttt acggttcctg    7320
gccttttgct ggccttttgc tcacatgttc tttcctgcgt tatcccctga ttctgtggat    7380
aaccgtatta ccgcctttga gtgagctgat accgctcgcc gcagccgaac gaccgagcgc    7440
agcgagtcag tgagcgagga agcggaagag cgcccaatac gcaaaccgcc tctccccgcg    7500
cgttggccga ttcattaatg                                                7520
```

<210> SEQ ID NO 8
<211> LENGTH: 90
<212> TYPE: DNA
<213> ORGANISM: Artificial Sequence
<220> FEATURE:
<223> OTHER INFORMATION: Synthetic Sequence [Insert - Before
      Belatacept]

<400> SEQUENCE: 8

```
ggtaccgcca ccatggccac cggctctcgc acaagcctgc tgctggcttt cggactgctg     60
tgcctgcctt ggctccagga gggctccgcc                                      90
```

<210> SEQ ID NO 9
<211> LENGTH: 742
<212> TYPE: DNA
<213> ORGANISM: Artificial Sequence
<220> FEATURE:
<223> OTHER INFORMATION: Synthetic Sequence [Insert - Between
      Belatacept and miR-E1]

<400> SEQUENCE: 9

```
ggatccggag gaggaggcag cggaggaggc ggatctggcg gaggcggaag cgacaagacc     60
cacacatgcc caccatgtcc tgcacctgaa ctcctggggg gaccgtcagt cttcctcttc    120
cccccaaaac ccaaggacac cctcatgatc tcccggaccc ctgaggtcac atgcgtggtg    180
gtggacgtga gccacgaaga ccctgaggtc aagttcaact ggtacgtgga cggcgtggag    240
gtgcataatg ccaagacaaa gccgcgggag gagcagtaca acagcacgta ccgtgtggtc    300
agcgtcctca ccgtcctgca ccaggactgg ctgaatggca aggagtacaa gtgcaaggtc    360
tccaacaaag ccctcccagc ccccatcgag aaaaccatct ccaaagccaa agggcagccc    420
cgagaaccac aggtgtacac cctgccccca tcccgggagg agatgaccaa gaaccaggtc    480
agcctgacct gcctggtcaa aggcttctat cccagcgaca tcgccgtgga gtgggagagc    540
aatgggcagc cggagaacaa ctacaagacc acgcctcccg tgctggactc cgacggctcc    600
```

```
ttcttcctct acagcaagct caccgtggac aagagcaggt ggcagcaggg gaacgtcttc     660
tcatgctccg tgatgcatga ggctctgcac aaccactaca cgcagaagag cctctccctg     720
tctccgggta aatagcgcta gc                                              742
```

```
<210> SEQ ID NO 10
<211> LENGTH: 6
<212> TYPE: DNA
<213> ORGANISM: Artificial Sequence
<220> FEATURE:
<223> OTHER INFORMATION: Synthetic Sequence  [Inverted Terminal Repeat -
      (Insert - After miR-E3)]

<400> SEQUENCE: 10 tctaga                                                                  6

<210> SEQ ID NO 11
<211> LENGTH: 22
<212> TYPE: DNA
<213> ORGANISM: Artificial Sequence
<220> FEATURE:
<223> OTHER INFORMATION: Synthetic Sequence  [S75428 Sense Strand]

<400> SEQUENCE: 11
cgctatctca taccaggaga aa                                               22

<210> SEQ ID NO 12
<211> LENGTH: 22
<212> TYPE: DNA
<213> ORGANISM: Artificial Sequence
<220> FEATURE:
<223> OTHER INFORMATION: Synthetic Sequence  [S75428 Antisense Strand]

<400> SEQUENCE: 12
tttctcctgg tatgagatag ca                                               22

<210> SEQ ID NO 13
<211> LENGTH: 22
<212> TYPE: DNA
<213> ORGANISM: Artificial Sequence
<220> FEATURE:
<223> OTHER INFORMATION: Synthetic Sequence  [S202295 Sense Strand]

<400> SEQUENCE: 13
acaaaccacc aagtggagga gc                                               22

<210> SEQ ID NO 14
<211> LENGTH: 22
<212> TYPE: DNA
<213> ORGANISM: Artificial Sequence
<220> FEATURE:
<223> OTHER INFORMATION: Synthetic Sequence  [S202295 Antisense Strand]

<400> SEQUENCE: 14
gctcctccac ttggtggttt gc                                               22

<210> SEQ ID NO 15
<211> LENGTH: 22
<212> TYPE: DNA
<213> ORGANISM: Artificial Sequence
<220> FEATURE:
<223> OTHER INFORMATION: Synthetic Sequence  [S75250 Sense Strand]

<400> SEQUENCE: 15
accaagtact tagactttgc gg                                               22
```

-continued

```
<210> SEQ ID NO 16
<211> LENGTH: 22
<212> TYPE: DNA
<213> ORGANISM: Artificial Sequence
<220> FEATURE:
<223> OTHER INFORMATION: Synthetic Sequence  [S75250 Antisense Strand]

<400> SEQUENCE: 16
ccgcaaagtc taagtacttg gg                                            22

<210> SEQ ID NO 17
<211> LENGTH: 125
<212> TYPE: PRT
<213> ORGANISM: Artificial Sequence
<220> FEATURE:
<223> OTHER INFORMATION: Synthetic Protein  [Belatacept Protein]

<400> SEQUENCE: 17

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln
        115                 120                 125
```

COMPOSITIONS AND METHODS FOR REGULATING PRODUCTION OF A FUSION PROTEIN AND RIBONUCLEIC ACID

TECHNICAL FIELD

The present disclosure generally relates to compositions and methods for regulating production of a fusion protein and ribonucleic acid (RNA). In particular, the present disclosure relates to compositions and methods for regulating gene expression and, therefore, production of a fusion protein and interfering RNA both of which relate to suppressing immune responses.

BACKGROUND

The mammalian immune system can differentiate between self and foreign matter. A number of cascades of signaling molecules and immune cells are characterized by their ability to recognize foreign matter and to call upon the production and stimulation of effector cells of the immune system to kill, break down, consume, or sheath the foreign matter in order to protect a host.

It is known that under various conditions the immune system can become dysregulated. A dysregulated immune system can cause further damage to the host, thereby preventing healing. It may also result in a loss of homeostatic controls and/or a chronically stimulated immune system.

Known approaches to the treatment of conditions whereby the immune system is dysregulated are the commercially available pharmaceutical products that bind to and block the production or effectiveness of one or more checkpoint molecules.

SUMMARY

Some embodiments of the present disclosure relate to compositions and methods that upregulate the production of a belatacept-similar protein (BSP). The BSP has a similar, substantially the same or the same biological function as belatacept when administered to a subject. In some embodiments the compositions comprise vector of plasmid deoxyribonucleic acid (DNA) that includes an insert sequence of nucleic acids that encode for the production of the BSP and a backbone sequence of nucleic acids that facilitate introduction of the insert sequence into one or more of a subject's cells where the insert sequence is expressed and/or replicated. Expression of the insert sequence by one or more cells of the subject results in an increased production of the BSP. In some embodiments of the present disclosure, the methods that upregulate the production of BSP relate to methods of manufacturing and administering the composition.

Some embodiments of the present disclosure relate to compositions and methods that upregulate the production of one or more sequences of interfering ribonucleic acid (RNA). The sequences of RNA may be complimentary to a sequence of target messenger RNA (mRNA) that encodes for translation of a target cytokine and the interfering RNA can cause the target mRNA to be degraded or inactivated, thereby causing a decrease in production of the target cytokine. In some embodiments of the present disclosure, the target cytokine is a pro-inflammatory cytokine, such as tumor necrosis factor alpha (TNF-alpha). In some embodiments of the present disclosure, the target cytokine is an anti-inflammatory cytokine. In some embodiments of the present disclosure the compositions comprise vector DNA that includes one or more an insert sequences of nucleic acids that encode for the production of interfering RNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the interfering RNA and, therefore, decreased translation of the target cytokine by one or more of the subject's cells. In some embodiments of the present disclosure, the methods that upregulate the production of the one or more interfering RNA sequences relate to methods of manufacturing and administering the composition.

Some embodiments of the present disclosure relate to compositions and methods that upregulate the production of both the BSP and interfering RNA that degrades, or causes degradation of, or inactivates or causes the inactivation of the mRNA of the target cytokine.

Some embodiments of the present disclosure relate to compositions and methods that can be used as a therapy or a treatment for a subject that has a condition whereby the subject's immune system is, or is likely to become, dysregulated.

Some embodiments of the present disclosure relate to a recombinant virus vector (RVV). The RVV comprises a nucleotide sequence encoding a belatacept-similar protein (BSP); one or more nucleotide sequences encoding an interfering ribonucleic acid (RNA) that targets messenger ribonucleic acid (mRNA) of tumor necrosis alpha (TNF-alpha); and an inverted terminal repeat.

Some embodiments of the present disclosure relate to a composition that comprises a nucleotide sequence according to the present disclosure (SEQ ID 7) that can be expressed in a target cell.

Some embodiments of the present disclosure relate to an insert for use with an RVV, wherein the insert has a nucleotide sequence according to SEQ ID 6.

Some embodiments of the present disclosure relate to a method of making an agent/target cell complex, the method comprising a step of administering a therapeutically effective amount of the agent to a subject, wherein the agent/target cell complex increases the subject's production of the BSP.

Some embodiments of the present disclosure relate to a method of making an agent/target cell complex, the method comprising a step of administering a therapeutically effective amount of the agent to a subject, wherein the agent/target cell complex increases the subject's production of one or more sequences of interfering RNA that decreases the production of a target cytokine.

Some embodiments of the present disclosure relate to a method of making an agent/target cell complex, the method comprising a step of administering a sufficient amount of an agent to a target cell whereby the agent/target cell complex is formed, wherein the agent/target cell complex increases the subject's production of the BSP and the agent/target cell complex also increases the subject's production of one or more sequences of interfering RNA that decreases the production of a target cytokine.

Some embodiments of the present disclosure relate to a pharmaceutical agent that comprises an agent, a pharmaceutically acceptable carrier and/or an excipient. Administering the pharmaceutical agent to a subject may increase the subject's production of the BSP, one or more sequences of interfering RNA that decreases the production of a target cytokine or both.

Some embodiments of the present disclosure relate to a method of treating a condition. The method comprises a step of administering to a subject a therapeutically effective amount of an agent that upregulates the subject's production of the BSP, one or more sequences of interfering RNA that decreases the production of a target cytokine or both.

Some embodiments of the present disclosure relate to a use of an agent for treating a condition, wherein the agent upregulates the subject's production of the BSP, one or more sequences of interfering RNA that decreases the production of a target cytokine or both.

Embodiments of the present disclosure relate to at least one approach for inducing endogenous production of the BSP and one or more sequences of interfering RNA that target the mRNA of TNF-alpha. A first approach utilizes gene vectors containing nucleotide sequences for increasing the endogenous production of BSP and one or more sequences of interfering RNA that target the mRNA of TNF-alpha, which can be administered to a subject to increase the subject's production of the BSP and one or more sequences of interfering RNA. Without being bound by any particular theory, embodiments of the present disclosure may be useful for treating conditions wherein the subject's immune system has become dysregulated.

BRIEF DESCRIPTION OF THE DRAWINGS

These and other features of the present disclosure will become more apparent in the following detailed description in which reference is made to the appended drawings.

FIG. 1 is a schematic that represents a first portion of a plasmid vector of SEQ ID 7, according to embodiments of the present disclosure.

FIG. 3 is a schematic that represents a third portion of a plasmid vector of SEQ ID 7, according to embodiments of the present disclosure, which is contiguous with the second portion of FIG. 2.

DETAILED DESCRIPTION

Figure 2:
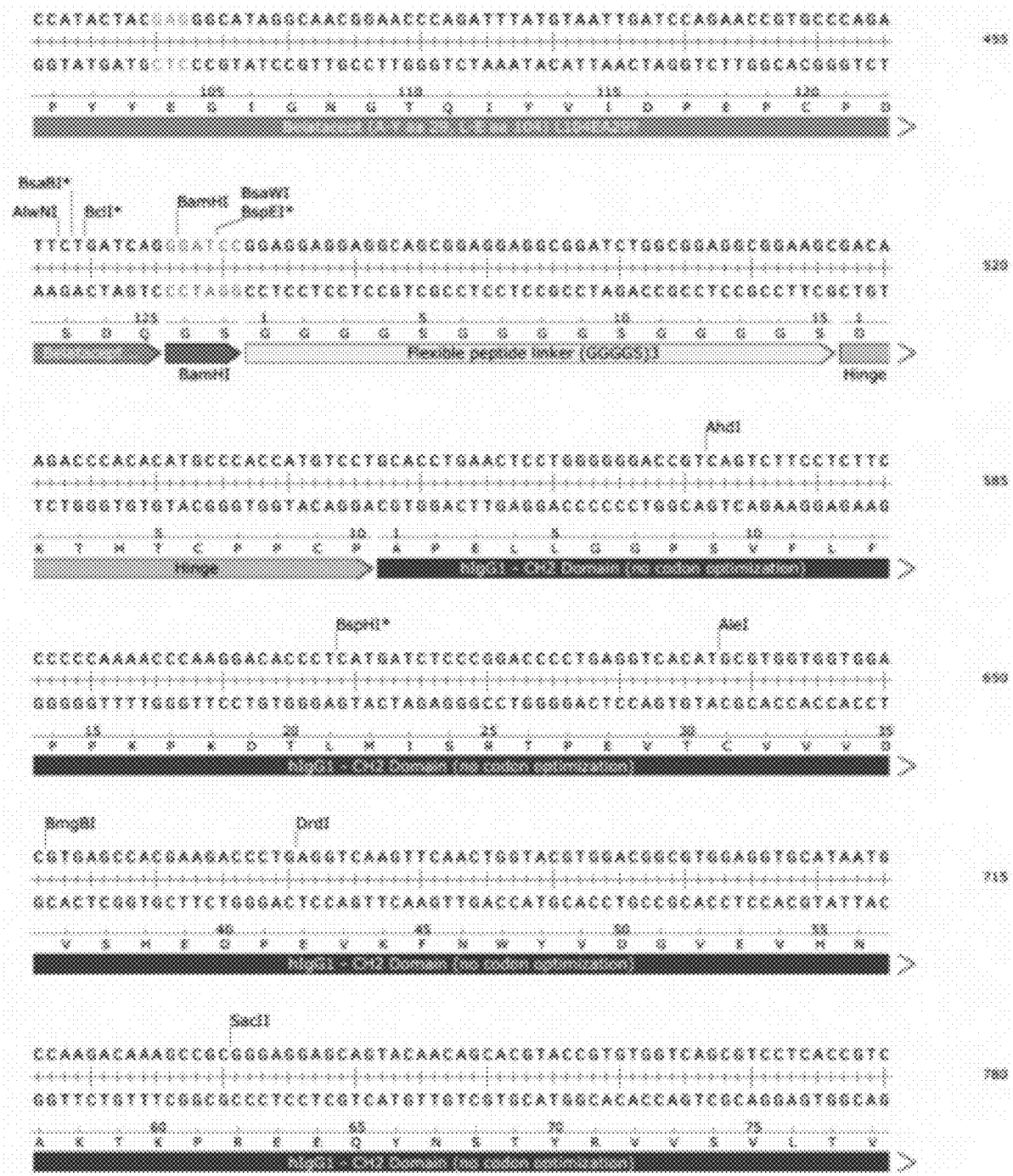
FIG. 2 is a schematic that represents a second portion of a plasmid vector of SEQ ID 7, according to embodiments of the present disclosure, which is contiguous with the first portion of FIG. 1.

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "activity" is used interchangeably with the term "functionality" and both terms refer to the physiologic action of biomolecule.

As used herein, the term "agent" refers to a substance that, when administered to a subject, causes one or more chemical reactions and/or one or more physical reactions and/or or one or more physiological reactions and/or one or more immunological reactions in the subject. In some embodiments of the present disclosure, the agent is a plasmid vector.

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite or another metabolite that is found within a subject. A biomolecule may be endogenous or exogenous to a subject.

As used herein, the term "cell" refers to a single cell as well as a plurality of cells or a population of the same cell type or different cell types. Administering an agent to a cell includes in vivo, in vitro and ex vivo administrations and/or combinations thereof.

As used herein, the term "complex" refers to an association, either direct or indirect, between one or more particles of an agent and one or more target cells. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, and/or any post-translational modifications of one or more proteins.

As used herein, the terms "dysregulation" and "dysregulated" refer to situations or conditions wherein homeostatic control systems have been disturbed and/or compromised so that one or more metabolic, physiologic and/or biochemical systems within a subject operate partially or entirely without said homeostatic control systems.

As used herein, the term "effector molecule" refers to a molecule within a subject that can directly or indirectly regulate the metabolic activity of a target cell by increasing or decreasing the production of DNA, RNA and/or amino-acid sequences and/or by increasing or decreasing any post-translational modifications of one or more proteins.

As used herein, the term "endogenous" refers to the production and/or modification of a molecule that originates within a subject.

As used herein, the term "excipient" refers to any substance, not itself an agent, which may be used as a component within a pharmaceutical composition or a medicament for administration of a therapeutically effective amount of the agent to a subject. Additionally, or alternatively, an excipient may, either alone or in combination with further chemical components, improve the handling and/or storage properties and/or permit or facilitate formation of a dose unit of the agent. Excipients include, but are not limited to, one or more of: a binder, a disintegrant, a diluent, a buffer, a taste enhancer, a solvent, a thickening agent, a gelling agent, a penetration enhancer, a solubilizing agent, a wetting agent, an antioxidant, a preservative, a surface active agent, a lubricant, an emollient, a substance that is added to mask or counteract a disagreeable odor, fragrance or taste, a substance added to improve appearance or texture of the composition and/or a substance that is used to form the pharmaceutical compositions or medicaments. Any such excipients can be used in any dosage forms according to the present disclosure. The foregoing classes of excipients are not meant to be exhaustive but are provided merely to be illustrative of what a person of skill in the art would know and would also recognize that additional types and combinations of excipients may be used to achieve delivery of a therapeutically effective amount of the agent to a subject through one or more routes of administration.

As used herein, the term "exogenous" refers to a molecule that is within a subject but that did not originate within the subject.

As used herein, the terms "inhibit". "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100, or any amount of reduction in between the specifically recited percentages, as compared to native or control levels.

As used herein, the term "medicament" refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the term "patient" refers to a subject that is afflicted with a disease or disorder. The term "patient" includes human and veterinary subjects.

As used herein, the term "pharmaceutical composition" means any composition comprising, but not necessarily limited to, an agent to be administered a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active ingredients such as antimicrobial agents, anti-inflammatory agents, anaesthetics, analgesics, and the like.

As used herein, the term "pharmaceutically acceptable carrier" refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company. Easton, PA), the disclosure of which is incorporated herein by reference. Typically, an appropriate amount of a pharmaceutically acceptable carrier is used in the formulation to render said formulation isotonic. Examples of suitable pharmaceutically acceptable carriers include, but are not limited to: saline solutions, glycerol solutions, ethanol, N-(1(2,3-dioleyloxy)propyl)-N,N,N-trimethylammonium chloride (DOTMA), dioleolphosphotidylethanolamine (DOPE), and liposomes. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require enteric coatings to protect the agent from degrading within portions of the subject's gastrointestinal tract. In another example, injectable routes of administration may be administered in a liposomal formulation to facilitate transport throughout a subject's vascular system and to facilitate delivery across cell membranes of targeted intracellular sites.

As used herein, the phrases "prevention of" and "preventing" refer to avoiding the onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also be used herein to refer to the functionality of a regulatory molecule, unless the context reasonably indicates otherwise.

As used herein, the terms "promote", "promotion", and "promoting" refer to an increase in an activity, response, condition, disease process, or other biological parameter. This can include, but is not limited to, the initiation of the activity, response, condition, or disease process. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term "prophylactic administration" refers to the administration of any composition to a subject, in the absence of any symptom or indication of a disease or disorder, to prevent the occurrence and/or progression of the disease or disorder within the subject.

As used herein, the terms "signal molecule", "signalling molecule" and "regulatory molecule" can be used interchangeably and refer to a molecule that can directly or indirectly affect the production and/or functionality of an effector molecule or effector cell. Signal molecules can be enzymes or other types of biomolecules that can act as a direct ligand on a target cell or they may influence the levels or functionality of a downstream ligand or a receptor for a ligand.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and for a sample of biological materials such as tissue and/or biological fluids.

As used herein, the term "target cell" refers to one or more cells and/or cell types that are deleteriously affected, either directly or indirectly, by a dysregulated immune system and/or a disease process. The term "target cell" also refers to cells that are not deleteriously affected but that are the cells in which it is desired that the agent interacts.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active ingredients, or combinations thereof. The amount of agent within each unit is a therapeutically effective amount.

In embodiments of the present disclosure, the pharmaceutical compositions disclosed herein comprise an agent as described above in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, an agent is a plasmid vector for introducing genes into a target cell for reproduction or transcription of an insert that comprises one or more nucleotide sequences that are carried within the plasmid vector. In some embodiments of the present disclosure, the plasmid vector is a viral vector. In some embodiments of the present disclosure, the vector is an adeno-associated virus vector.

In some embodiments of the present disclosure, the insert comprises one or more nucleotide sequences that encode for production of at least a belatacept similar protein (BSP).

The BSP has physiologic/biologic equivalence to belatacept, meaning the BSP will have substantially the same effect on the subject or target cell as a similar dose of belatacept will. Beletacept is a known immunosuppressant that is used to reduce rejection in recipients of organ transplants. Similar to belatacept, BSP is a fusion protein that combines an Fc portion of a human immunoglobulin IgG1 with an extracellular portion of cytotoxic T-lymphocyte-associated protein 4 (CTLA-4). Belatacept can interfere with binding of antigen presenting cells and, therefore, belatacept can prevent activation of T-cells. As such, the BSP may also prevent activation of T-cells.

In some embodiments of the present disclosure, the insert comprises one or more nucleotide sequences that encode for production of at least one sequence of interfering RNA that decreases the production of target cytokine proteins. The interfering RNA may, directly or indirectly, bind to and degrade the target mRNA or otherwise inactivate the target mRNA so that less or none of the target-cytokine protein is produced. In some embodiments of the present disclosure, the interfering RNA may be short-interfering RNA (siRNA), microRNA (miRNA) or combinations thereof.

In some embodiments of the present disclosure, the target cytokine is a pro-inflammatory cytokine, meaning it has the physiologic effect of increasing inflammatory processes in the subject. In some embodiments of the present disclosure, the target cytokine is TNF-alpha. In some embodiments of the present disclosure, the target cytokine is an anti-inflammatory cytokine.

In some embodiments of the present disclosure, the insert comprises two or more nucleotide sequences that each encode one or more interfering RNA sequences that may be complimentary to and degrades, or causes degradation of, mRNA of the target cytokine. In some embodiments of the present disclosure the insert comprises three nucleotide sequences that each encode an interfering RNA sequence that may be complimentary to and degrade, or causes degradation of, or inactivates or causes inactivation of mRNA of the target cytokine.

In some embodiments of the present disclosure, the insert comprises one or more nucleotide sequences that encode for production of the BSP and one or more nucleotide sequences that each encode for an interfering RNA sequence that may be complimentary to and degrades, or causes degradation of, or inactivates or causes inactivation of mRNA of the target cytokine. In some embodiments of the present disclosure, the insert comprises three nucleotide sequences that each encode for interfering RNA that may be complimentary to and degrade, or causes degradation of, or inactivate, or causes inactivation of mRNA of the target cytokine.

The present disclosure relates to one or more agents, therapies, treatments, and methods of use of the agents and/or therapies and/or treatments for initiating or upregulating production of the BSP while downregulating production and/or functionality of the target cytokine. Some embodiments of the present disclosure relate to methods for making a complex between at least one particle of an agent and at least one target cell of a subject for initiating or increasing production of the BSP and for downregulating the subject's production and/or functionality of the target cytokine. Embodiments of the present disclosure can be used as a therapy or a treatment for a subject that has a condition whereby the subject's immune system is, or is likely to become, dysregulated.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, and combinations thereof.

In some embodiments of the present disclosure, the agent can be administered to the subject by pipetting a dose of the agent into an in vitro cell culture, perfusing or immersing an ex vivo cell or tissue preparation with a solution that comprises the agent, mixing a biological fluid sample with a solution or substrate that comprises the agent, or combinations thereof.

Some embodiments of the present disclosure relate to an agent that can be administered to a subject with the condition. When a therapeutically effective amount of the agent is administered to the subject, the subject may change production and/or functionality of one or more immune system molecules. For example, the subject may decrease production and/or functionality of one or more immune system signaling molecules and/or one or more immune system effector molecules by changing the production of one or more sequences of DNA, one or more sequences of RNA and/or one or more proteins and/or one or more regulatory molecules that regulate the levels and/or functionality of the subject's immune system signaling molecules and/or immune system effector molecules.

In some embodiments of the present disclosure, the subject may respond to receiving the therapeutic amount of the agent by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more immune system signaling molecules and/or the one or more immune system effector molecules.

In some embodiments of the present disclosure, administering a therapeutic amount of the agent to a subject upregulates the production, functionality or both of the BSP and one or more sequences of interfering RNA that each target the mRNA of one or more target cytokines. Examples of the target cytokine include one or more pro-inflammatory cytokines, one or more anti-inflammatory cytokines or combinations thereof. In some embodiments of the present disclosure, there are one, two three, four, five, six, seven, eight, nine or ten interfering RNA sequences that each are complimentary to and degrade, or cause degradation of, one cytokine, such as TNF-alpha. In some embodiments of the present disclosure, the agent may comprise multiple copies of the same nucleotide sequence of interfering RNA.

In some embodiments of the present disclosure, the agent is a vector used for gene therapy. The gene therapy is useful for increasing the subject's endogenous production of the BSP and one or more sequences of interfering RNA that target the mRNA of a target cytokine. For example, the vector can contain one or more nucleotide sequences that that cause increased production of the BSP and increased production of one or more interfering RNA sequences that that each are complimentary to and degrade, or cause degradation of, or inactivate, or cause inactivation of one cytokine, such as TNF-alpha.

In some embodiments of the present disclosure, the vector used for gene therapy is a virus that can be enveloped or not, replication effective or not, or combinations thereof. In some embodiments of the present disclosure, the vector is a virus that is not enveloped and not replication effective. In some embodiments of the present disclosure, the vector is a virus of the Paroviridae family. In some embodiments of the present disclosure, the vector is a virus of the genus Dependoparvaovirus. In some embodiments of the present disclosure, the vector is an adeno-associated virus (AAV). In some embodiments of the present disclosure, the vector is a recombinant AAV.

The embodiments of the present disclosure also relate to administering a therapeutically effective amount of the agent. In some embodiments of the present disclosure, the therapeutically effective amount of the agent that is administered to a patient is between about 10 and about $1 \times 10^{16}$ $TCID_{50}$/kg (50% tissue culture infective dose per kilogram of the patient's body weight). In some embodiments of the present disclosure, the therapeutically effective amount of the agent that is administered to the patient is about $1 \times 10^{13}$ $TCID_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1 \times 10^{16}$ TCP/kg.

Some embodiments of the present disclosure relate to a method for making a complex within a subject. The method comprises a step of administering a therapeutically effective amount of the agent to the subject. The complex comprises at least one particle of agent and one or more target cells. When the complex is formed, it affects a change in metabolism of the one or more target cells, which results in the subject upregulating the production of the BSP and one or more sequences of interfering RNA that target the mRNA of a target cytokine, such as TNF-alpha. Examples of a target cell include, but are not limited to: an adrenal gland cell; a B cell; a bile duct cell; a chondrocyte; a cochlear cell; a corneal cell; an endocardium cell; an endometrial cell; an endothelial cell; an epithelial cell; an eosinophil; a fibroblast; a hair follicle cell; a hepatocyte; a lymph node cell; a macrophage; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a T cell; a testicular tissue cell; a thyroid gland cell; a uveal cell; or combinations thereof.

Some embodiments of the present disclosure relate to a therapy, or method of treating a condition, that can be administered to a subject with the condition. The therapy comprises a step of administering to the subject a therapeutically effective amount of an agent that will upregulate the subject's production of the BSP and one or more sequences of interfering RNA that target the mRNA of a target cytokine, such as TNF-alpha The increased production of the BSP and increased production of the interfering RNA may reduce deleterious effects of the condition upon the subject.

Below are examples of nucleotide sequences of each may be present in the insert. As will be appreciated by those skilled in the art, minor modifications, substitutions or replacements of a select few nucleotides or amino acids in the sequences provided below will not substantially impact the physiologic or biologic effect of such modified sequences, as compared to the sequences provided herein below. Any such modified sequences are also contemplated by the present disclosure.

(nucleotide sequence for BSP)

SEQ ID 1

```
atgcacgtgg cccagcctgc tgtggtactg gccagcagcc gaggcatcgc cagctttgtg    60
tgtgagtatg catctccagg caaatacact gaggtccggg tgacagtgct tcggcaggct   120
gacagccagg tgactgaagt ctgtgcggca acctacatga tggggaatga gttgaccttc   180
ctagatgatt ccatctgcac gggcacctcc agtggaaatc aagtgaacct cactatccaa   240
ggactgaggg ccatggacac gggactctac atctgcaagg tggagctcat gtacccaccg   300
ccatactacg agggcatagg caacggaacc cagatttatg taattgatcc agaaccgtgc   360
ccagattctg atcag                                                    375
```

(nucleotide sequence for interfering RNA-E1 protein)

SEQ ID 2

```
cgacttctta acccaacaga aggctcgaga aggtatattg ctgttgacag tgagcgcgct    60
atctcatacc aggagaaata gtgaagccac agatgtattt ctcctggtat gagatagcat   120
gcctactgcc tcggacttca aggggctaga attcg
```

(nucleotide sequence for interfering RNA-E2 protein)

SEQ ID 3

```
cgacttctta acccaacaga aggctcgaga aggtatattg ctgttgacag tgagcgacaa    60
accaccaagt ggaggagcta gtgaagccac agatgtagct cctccacttg gtggtttgct   120
gcctactgcc tcggacttca aggggctaga attcg                              155
```

(nucleotide sequence for interfering RNA-E3 protein)

SEQ ID 4

```
cgacttctta acccaacaga aggctcgaga aggtatattg ctgttgacag tgagcgacca    60
agtacttaga ctttgcggta gtgaagccac agatgtaccg caaagtctaa gtacttgggt   120
gcctactgcc tcggacttca aggggctaga attcg                              155
```

(nucleotide sequence for interfering RNA-E1, 2 and 3 proteins)

SEQ ID 5

```
cgacttctta acccaacaga aggctcgaga aggtatattg ctgttgacag tgagcgcgct    60
atctcatacc aggagaaata gtgaagccac agatgtattt ctcctggtat gagatagcat   120
gcctactgcc tcggacttca aggggctaga attcgcgact tcttaaccca acagaaggct   180
cgagaaggta tattgctgtt gacagtgagc gacaaaccac caagtggagg agctagtgaa   240
gccacagatg tagctcctcc acttggtggt ttgctgccta ctgcctcgga cttcaagggg   300
ctagaattcg cgacttctta acccaacaga aggctcgaga aggtatattg ctgttgacag   360
tgagcgacca agtacttaga ctttgcggta gtgaagccac agatgtaccg caaagtctaa   420
gtacttgggt gcctactgcc tcggacttca aggggctaga attcg                   465
```

(nucleotide sequence for insert with BSP, interfering RNA-E1,
2 and 3 proteins)

SEQ ID 6

```
ggtaccgcca ccatggccac cggctctcgc acaagcctgc tgctggcttt cggactgctg    60
tgcctgcctt ggctccagga gggctccgcc atgcacgtgg cccagcctgc tgtggtactg   120
gccagcagcc gaggcatcgc cagctttgtg tgtgagtatg catctccagg caaatacact   180
gaggtccggg tgacagtgct tcggcaggct gacagccagg tgactgaagt ctgtgcggca   240
acctacatga tggggaatga gttgaccttc ctagatgatt ccatctgcac gggcacctcc   300
agtggaaatc aagtgaacct cactatccaa ggactgaggg ccatggacac gggactctac   360
atctgcaagg tggagctcat gtacccaccg ccatactacg agggcatagg caacggaacc   420
cagatttatg taattgatcc agaaccgtgc ccagattctg atcagggatc cggaggagga   480
ggcagcggag gaggcggatc tggcggaggc ggaagcgaca agacccacac atgcccacca   540
tgtcctgcac ctgaactcct gggggaccg tcagtcttcc tcttcccccc aaaacccaag   600
```

-continued

```
gacaccctca tgatctcccg gacccctgag gtcacatgcg tggtggtgga cgtgagccac   660
gaagaccctg aggtcaagtt caactggtac gtggacggcg tggaggtgca taatgccaag   720
acaaagccgc gggaggagca gtacaacagc acgtaccgtg tggtcagcgt cctcaccgtc   780
ctgcaccagg actggctgaa tggcaaggag tacaagtgca aggtctccaa caaagccctc   840
ccagccccca tcgagaaaac catctccaaa gccaagggc agccccgaga ccacaggtg    900 tacaccctgc ccccatcccg ggaggagatg accaagaacc aggtcagcct gacctgcctg   960
gtcaaaggct tctatcccag cgacatcgcc gtggagtggg agagcaatgg gcagccggag  1020
aacaactaca agaccacgcc tcccgtgctg gactccgacg gctccttctt cctctacagc  1080
aagctcaccg tggacaagag caggtggcag caggggaacg tcttctcatg ctccgtgatg  1140
catgaggctc tgcacaacca ctacacgcag aagagcctct ccctgtctcc gggtaaatag  1200
cgctagccga cttcttaacc caacagaagg ctcgagaagg tatattgctg ttgacagtga  1260
gcgcgctatc tcataccagg agaaatagtg aagccacaga tgtatttctc ctggtatgag  1320
atagcatgcc tactgcctcg gacttcaagg ggctagaatt cgcgacttct aacccaaca   1380 gaaggctcga gaaggtatat tgctgttgac agtgagcgac aaaccaccaa gtggaggagc  1440
tagtgaagcc acagatgtag ctcctccact tggtggtttg ctgcctactg cctcggactt  1500
caaggggcta gaattcgcga cttcttaacc caacagaagg ctcgagaagg tatattgctg  1560
ttgacagtga gcgaccaagt acttagactt tgcggtagtg aagccacaga tgtaccgcaa  1620
agtctaagta cttgggtgcc tactgcctcg gacttcaagg ggctagaatt cgtctagaa   1679
```

(expression cassette with insert)
SEQ ID 7

```
cagcagctgc gcgctcgctc gctcactgag gccgcccggg caaagcccgg gcgtcgggcg    60
acctttggtc gcccggcctc agtgagcgag cgagcgcgca gagagggagt ggccaactcc   120
atcactaggg gttccttgta gttaatgatt aacccgccat gctacttatc tacgtagcca   150
tgctctagga cattgattat tgactagtgg agttccgcgt tacataactt acggtaaatg   240
gcccgcctgg ctgaccgccc aacgaccccc gcccattgac gtcaataatg acgtatgttc   300
ccatagtaac gccaataggg actttccatt gacgtcaatg ggtggagtat ttacggtaaa   360
ctgcccactt ggcagtacat caagtgtatc atatgccaag tacgccccct attgacgtca   420
atgacggtaa atggcccgcc tggcattatg cccagtacat gaccttatgg gactttccta   480
cttggcagta catctacgta ttagtcatcg ctattaccat ggtcgaggtg agccccacgt   540
tctgcttcac tctccccatc tcccccccct ccccaccccc aatttigtat ttatttattt   600 tttaattatt ttgtgcagcg atggggggcgg ggggggggggg gggcgcgcgc caggcgggggc  660 ggggcggggc gaggggcggg gcggggcgag gcggagaggt gcggcggcag ccaatcagag   720
cggcgcgctc cgaaagtttc ctttatggc gaggcggcgg cggcggcggc cctataaaaa   780
gcgaagcgcg cggcgggcgg gagtcgctgc gcgctgcctt cgccccgtgc cccgctccgc   840
cgccgcctcg cgccgcccgc cccggctctg actgaccgcg ttactaaaac aggtaagtcc   900
ggcctccgcg ccgggttttg gcgcctcccg cgggcgcccc cctcctcacg gcgagcgctg   960
ccacgtcaga cgaagggcgc agcgagcgtc ctgatccttc cgcccggacg ctcaggacag  1020
cggcccgctg ctcataagac Icggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtgggcggt gaacgccgat   1200 gatgcctcta ctaaccatgt tcatgttttc ttttttttc tacaggtcct gggtgacgaa   1260
cagggtaccg ccaccatggc caccggctct cgcacaagcc Igctgctggc tttcggactg  1320
```

-continued

```
ctgtgcctgc cttggctcca ggagggctcc gccatgcacg tggcccagcc tgctgtggta 1380
ctggccagca gccgaggcat cgccagcttt gtgtgtgagt atgcatctcc aggcaaatac 1440
actgaggtcc gggtgacagt gcttcggcag gctgacagcc aggtgactga agtctgtgcg 1500
gcaacctaca tgatggggaa tgagttgacc ttcctagatg attccatctg cacgggcacc 1560
tccagtggaa atcaagtgaa cctcactatc caaggactga gggccatgga cacgggactc 1620
tacatctgca aggtggagct catgtaccca ccgccatact acgagggcat aggcaacgga 1680
acccagattt atgtaattga tccagaaccg tgcccagatt ctgatcaggg atccggagga 1740
ggaggcagcg gaggaggcgg atctggcgga ggcggaagcg acaagaccca cacatgccca 1800
ccatgtcctg cacctgaact cctgggggga ccgtcagtct tcctcttccc cccaaaaccc 1860
aaggacaccc tcatgatctc ccggacccct gaggtcacat gcgtggtggt ggacgtgagc 1920
cacgaagacc ctgaggtcaa gttcaactgg tacgtggacg gcgtggaggt gcataatgcc 1980
aagacaaagc cgcgggagga gcagtacaac agcacgtacc gtgtggtcag cgtcctcacc 2040
gtcctgcacc aggactggct gaatggcaag gagtacaagt gcaaggtctc caacaaagcc 2100
ctcccagccc ccatcgagaa aaccatctcc aaagccaaag gcagccccg agaaccacag 2160 gtgtacaccc tgcccccatc ccgggaggag atgaccaaga accaggtcag cctgacctgc 2220
ctggtcaaag gcttctatcc cagcgacatc gccgtggagt gggagagcaa tgggcagccg 2280
gagaacaact acaagaccac gcctcccgtg ctggactccg acggctcctt cttcctctac 2340
agcaagctca ccgtggacaa gagcaggtgg cagcagggga acgtcttctc atgctccgtg 2400
atgcatgagg ctctgcacaa ccactacacg cagaagagcc tctccctgtc tccgggtaaa 2460
tagcgctagc cgacttctta acccaacaga aggctcgaga aggtatattg ctgttgacag 2520
tgagcgcgct atctcatacc aggagaaata gtgaagccac agatgtattt ctcctggtat 2580
gagatagcat gcctactgcc tcggacttca aggggctaga attcgcgact tcttaaccca 2640
acagaaggct cgagaaggta tattgctgtt gacagtgagc gacaaaccac caagtggagg 2700
agctagtgaa gccacagatg tagctcctcc acttggtggt ttgctgccta ctgcctcgga 2760
cttcaagggg ctagaattcg cgacttctta acccaacaga aggctcgaga aggtatattg 2820
ctgttgacag tgagcgacca agtacttaga cttttgcggta gtgaagccac agatgtaccg 2880
caaagtctaa gtacttgggt gcctactgcc tcggacttca aggggctaga attcgtctag 2940
aataatcaac ctctggatta caaaatttgt gaaagattga ctggtattct taactatgtt 3000 gctccttta cgctatgtgg atacgctgct ttaatgcctt tgtatcatgc tattgcttcc 3060
cgtatggctt tcattttctc ctccttgtat aaatcctggt tgctgtctct ttatgaggag 3120
ttgtggcccg ttgtcaggca acgtggcgtg gtgtgcactg tgtttgctga cgcaaccccc 3180
actggttggg gcattgccac cacctgtcag ctcctttccg gactttcgc tttccccctc 3240 cctattgcca cggcggaact catcgccgcc tgccttgccc gctgctggac aggggctcgg 3300
ctgttgggca ctgacaattc cgtggtgttg tcggggaaat catcgtcctt ccttggctg 3360 ctcgcctgtg ttgccacctg gattctgcgc gggacgtcct tctgctacgt cccttcggcc 3420
ctcaatccag cggaccttcc ttcccgcggc ctgctgccgg ctctgcggcc tcttccgcgt 3480
cttcgccttc gccctcagac gagtcggatc tccctttggg ccgcctcccc gcctaagctt 3540
atcgataccg tcgagatcta acttgtttat tgcagcttat aatggttaca aataaagcaa 3600
tagcatcaca aatttcacaa ataaagcatt ttttcactg cattctagtt gtggtttgtc 3660
caaactcatc aatgtatctt atcatgtctg gatctcgacc tcgactagag catggctacg 3720
```

```
tagataagta gcatggcggg ttaatcatta actacaagga acccctagtg atggagttgg   3780
ccactccctc tctgcgcgct cgctcgctca ctgaggccgg gcgaccaaag gtcgcccgac   3840
gcccgggctt tgcccgggcg gcctcagtga gcgagcgagc gcgccagctg gcgtaatagc   3900
gaagaggccc gcaccgatcg cccttcccaa cagttgcgca gcctgaatgg cgaatggaat   3960
tccagacgat tgagcgtcaa aatgtaggta tttccatgag cgttttcct gttgcaatgg   4020 ctggcggtaa tattgttctg gatattacca gcaaggccga tagtttgagt tcttctactc   4080
aggcaagtga tgttattact aatcaaagaa gtattgcgac aacggttaat ttgcgtgatg   4140
gacagactct tttactcggt ggcctcactg attataaaaa cacttctcag gattctggcg   4200
taccgttcct gtctaaaatc cctttaatcg gcctcctgtt tagctcccgc tctgattcta   4260
acgaggaaag cacgttatac gtgctcgtca aagcaaccat agtacgcgcc ctgtagcggc   4320
gcattaagcg cggcgggtgt ggtggttacg cgcagcgtga ccgctacact tgccagcgcc   4380
ctagcgcccg ctcctttcgc tttcttccct cctttctcg ccacgttcgc cggctttccc   4440
cgtcaagctc taaatcgggg gctcccttta gggttccgat ttagtgcttt acggcacctc   4500
gaccccaaaa aacttgatta gggtgatggt tcacgtagtg ggccatcgcc ctgatagacg   4560 gttttttcgcc ctttgacgtt ggagtccacg ttctttaata gtggactctt gttccaaact   4620
ggaacaacac tcaaccctat ctcggtctat tcttttgatt tataagggat tttgccgatt   4680
tcggcctatt ggttaaaaaa tgagctgatt taacaaaaat ttaacgcgaa ttttaacaaa   4740
atattaacgt ttacaattta atatttgct tatacaatct tcctgttttt ggggcttttc   4800
tgattatcaa ccgggtaca tatgattgac atgctagttt tacgattacc gttcatcgat   4860
tctcttgttt gctccagact ctcaggcaat gacctgatag cctttgtaga gacctctcaa   4920
aaatagctac cctctccggc atgaatttat cagctagaac ggttgaatat catattgatg   4980
gtgatttgac tgtctccggc ctttctcacc cgtttgaatc tttacctaca cattactcag   5040 gcattgcatt (aaaatatat gagggttcta aaaattttta tccttgcgtt gaaataaagg   5100
cttctcccgc aaaagtatta cagggtcata atgtttttgg tacaaccgat ttagctttat   5160
gctctgaggc tttattgctt aattttgcta attctttgcc ttgcctgrat gatttattgg   5220
atgttggaat tcctgatgcg gtattttctc cttacgcatc tgtgcggtat ttcacaccgc   5280
atatggtgca ctctcagtac aatctgctct gatgccgcat agttaagcca gccccgacac   5340
ccgccaacac ccgctgacgc gccctgacgg gcttgtctgc tcccggcatc cgcttacaga   5400
caagctgtga ccgtctccgg gagctgcatg tgtcagaggt tttcaccgtc atcaccgaaa   5460
cgcgcgagac gaaagggcct cgtgatacgc ctatttttat aggttaatgt catgataata   5520
atggtttctt agacgtcagg tggcactttt cggggaaatg tgcgcggaac ccctatttgt   5580
ttatttttct aaatacattc aaatatgtat ccgctcatga caataaacc ctgataaatg   5640 cttcaataat attgaaaaag gaagagtatg agtattcaac atttccgtgt cgcccttatt   5700 ccctttttg cggcattttg ccttcctgtt tttgctcacc cagaaacgct ggtgaaagta   5760
aaagatgctg aagatcagtt gggtgcaoga gtgggttaca tcgaactgga tctcaacagc   5820
ggtaagatcc ttgagagttt cgccccgaa gaacgttttc caatgatgag cacttttaaa   5880
gttctgctat gtggcgcggt attatcccgt attgacgccg gcaagagca actcggtcgc   5940 cgcatacact attctcagaa tgacttggtt gagtactcac cagtcacaga aaagcatctt   6000
acggatggca tgacagtaag agaattatgc agtgctgcca taaccatgag tgataacact   6060
gcggccaact tacttctgac aacgatcgga ggaccgaagg agctaaccgc ttttttgcac   6120
aacatggggg atcatgtaac tcgccttgat cgttgggaac cggagctgaa tgaagccata   6180
```

-continued

```
ccaaacgacg agcgtgacac cacgatgcct gtagcaatgg caacaacgtt gcgcaaacta    6240
ttaactggcg aactacttac tctagcttcc cggcaacaat taatagactg gatggaggcg    6300
gataaagttg caggaccact tctgcgctcg gcccttccgg ctggctggtt tattgctgat    6360
aaatctggag ccgtgagcg tgggtctcgc ggtatcattg cagcactggg gccagatggt    6420
aagccctccc gtatcgtagt tatctacacg acggggagtc aggcaactat ggatgaacga    6480
aatagacaga tcgctgagat aggtgcctca ctgattaagc attggtaact gtcagaccaa    6540
gtttactcat atatacttta gattgattta aaacttcatt tttaatttaa aaggatctag    6600
gtgaagatcc ttttgataa tctcatgacc aaaatccctt aacgtgagtt ttcgttccac    6660
tgagcgtcag accccgtaga aagatcaaa ggatcttctt gagatccttt ttttctgcgc    6720
gtaatctgct gcttgcaaac aaaaaaacca ccgctaccag cggtggtttg tttgccggat    6780
caagagctac caactctttt tccgaaggta actggcttca gcagagcgca gataccaaat    6840
actgtccttc tagtgtagcc gtagttaggc caccacttca agaactctgt agcaccgcct    6900
acatacctcg ctctgctaat cctgttacca gtggctgctg ccagtggcga taagtcgtgt    6960
cttaccgggt tggactcaag acgatagtta ccggataagg cgcagcggtc gggctgaacg    7020
gggggttcgt gcacacagcc cagcttggag cgaacgacct acaccgaact gagataccta    7080
cagcgtgagc tatgagaaag cgccacgctt cccgaaggga gaaaggcgga caggtatccg    7140
gtaagcggca gggtcggaac aggagagcgc acgagggagc ttccaggggg aaacgcctgg    7200
tatctttata gtcctgtcgg gtttcgccac ctctgacttg agcgtcgatt tttgtgatgc    7260
tcgtcagggg gcggagcct atggaaaaac gccagcaacg cggcctttt acggttcctg    7320
gccttttgct ggccttttgc tcacatgttc tttcctgcgt tatcccctga ttctgtggat    7380
aaccgtatta ccgcctttga gtgagctgat accgctcgcc gcagccgaac gaccgagcgc    7440
agcgagtcag tgagcgagga agcggaagag cgcccaatac gcaaaccgcc tctccccgcg    7500
cgttggccga ttcattaatg                                                7520
```

(expression cassette start to BSP region)   SEQ ID 8
```
ggtaccgcca ccatggccac cggctctcgc acaagcctgc tgctggcttt cggactgctg     60
tgcctgcctt ggctccagga gggctccgcc                                      90
```

(expression cassette end of BSP region to interfering R-E1)   SEQ ID 9
```
ggatccggag gaggaggcag cggaggaggc ggatctggcg gaggcggaag cgacaagacc     60
cacacatgcc caccatgtcc tgcacctgaa ctcctggggg gaccgtcagt cttcctcttc    120
cccccaaaac ccaaggacac cctcatgatc tcccggaccc ctgaggtcac atgcgtggtg    180
gtggacgtga gccacgaaga ccctgaggtc aagttcaact ggtacgtgga cggcgtgag    240
gtgcataatg ccaagacaaa gccgcgggag gagcagtaca acagcacgta ccgtgtggtc    300
agcgtcctca ccgtcctgca ccaggactgg ctgaatggca aggagtacaa gtgcaaggtc    360
tccaacaaag ccctcccagc ccccatcgag aaaaccatct ccaaagccaa agggcagccc    420
cgagaaccac aggtgtacac cctgccccca tcccggagg atgaccaa gaaccaggtc    480
agcctgacct gcctggtcaa aggcttctat cccagcgaca tcgccgtgga gtgggagagc    540
aatgggcagc cggagaacaa ctacaagacc acgcctcccg tgctggactc cgacggctcc    600
ttcttcctct acagcaagct caccgtggac aagagcaggt ggcagcaggg gaacgtcttc    660
tcatgctccg tgatgcatga ggctctgcac aaccactaca cgcagaagag cctctccctg    720
tctccgggta aatagcgcta gc                                             742
```

```
                                            SEQ ID 10
(inverted terminal repeat)
tctaga                                      6

(amino acid sequence for BSP produced per SEQ ID 1)
                                            SEQ ID 11
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala The Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln
        115                 120                 125
```

Example 1—Expression Cassette

Figure 1:
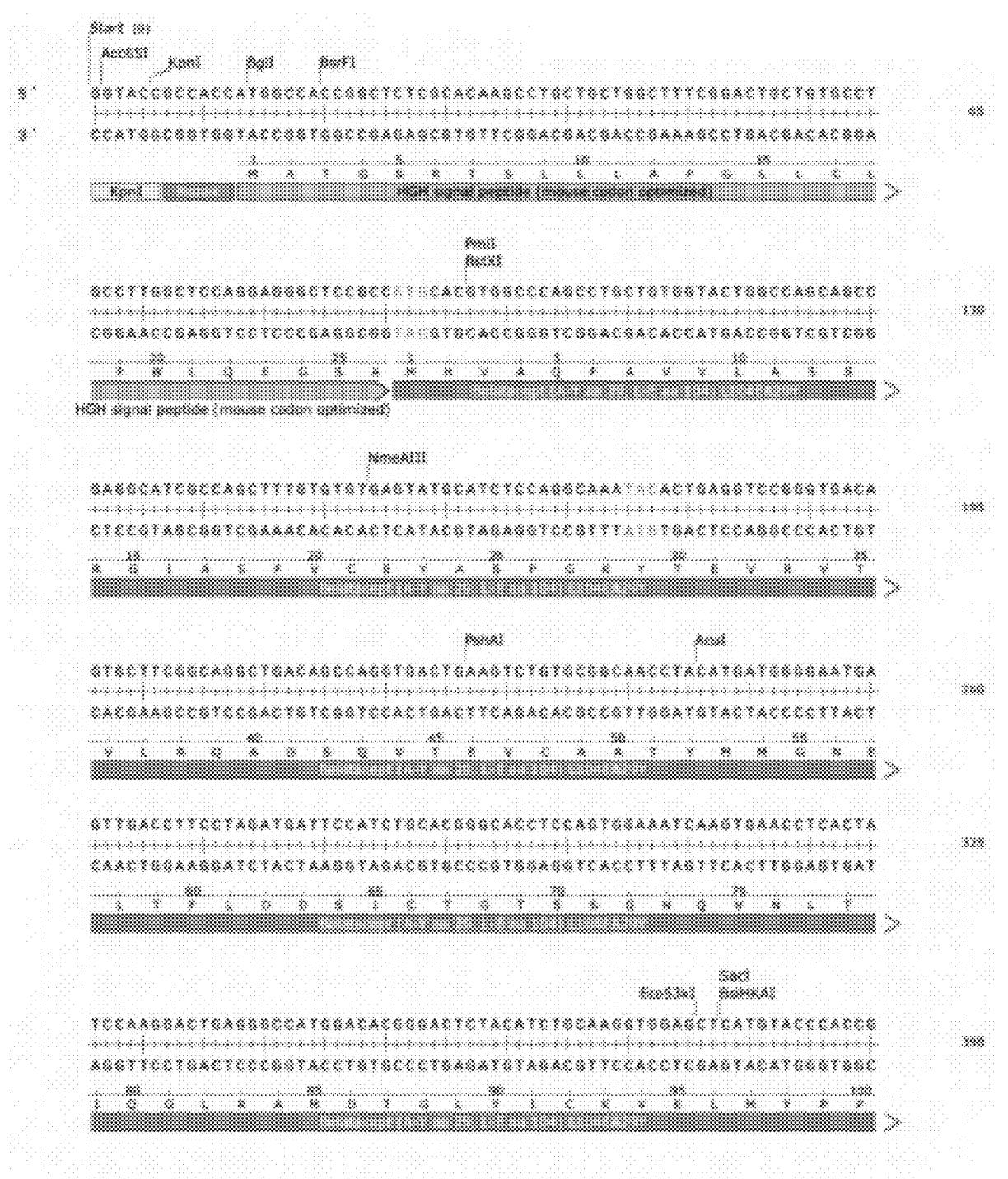
Figure 3:
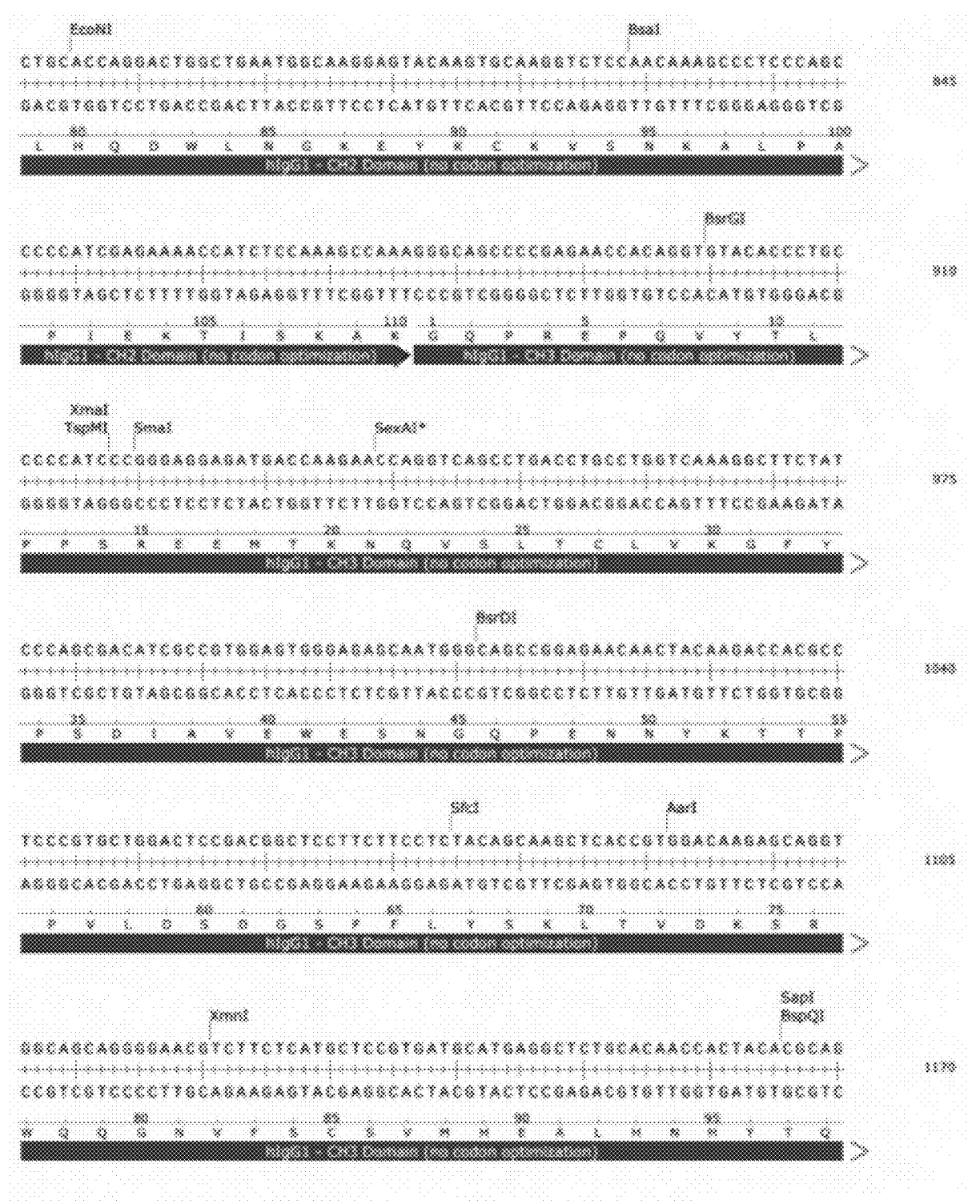
Figure 4:
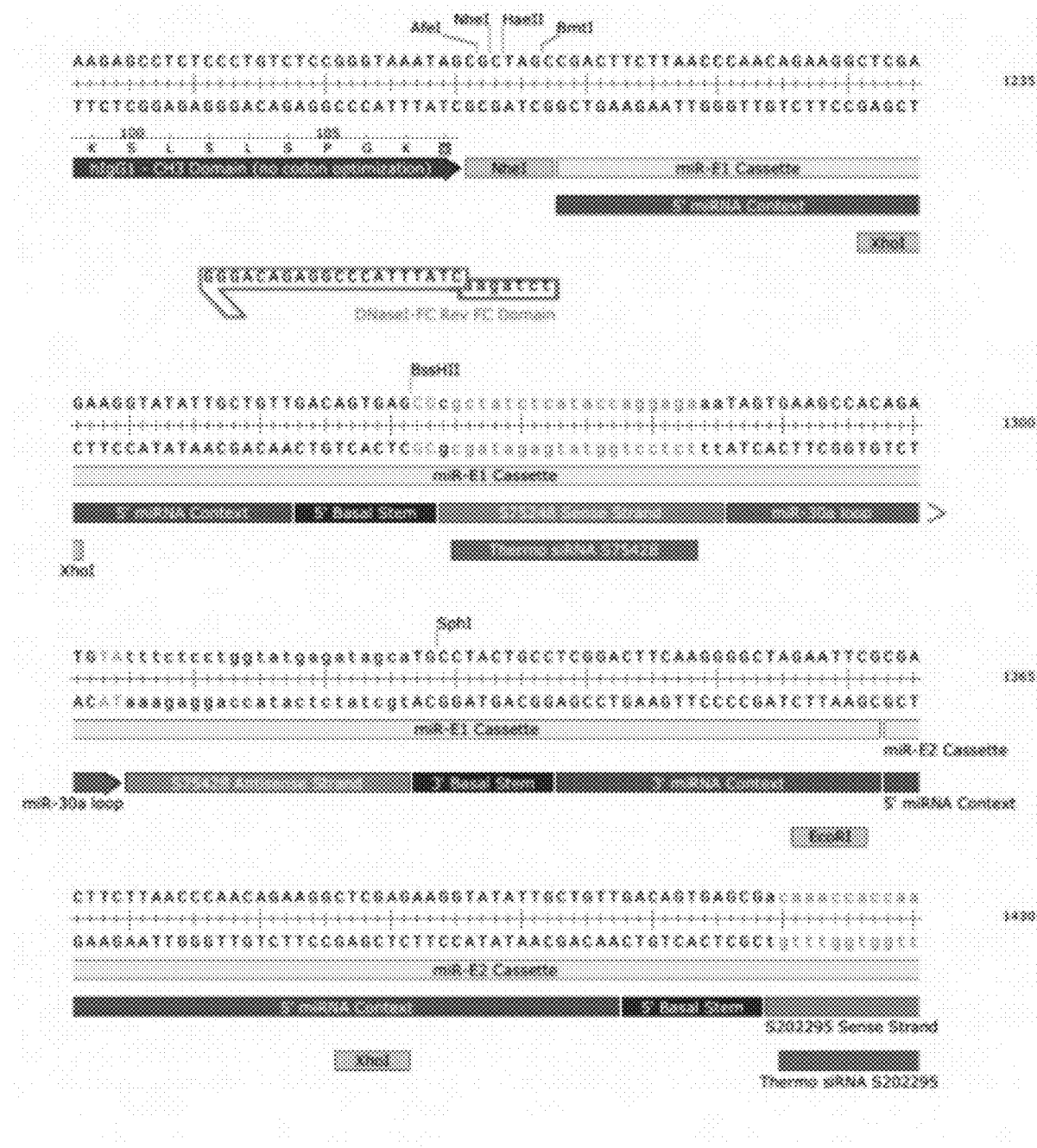
FIG. 4 is a schematic that represents a fourth portion of a plasmid vector of SEQ ID 7, according to embodiments of the present disclosure, which is contiguous with the third portion of FIG. 3.
Figure 5:
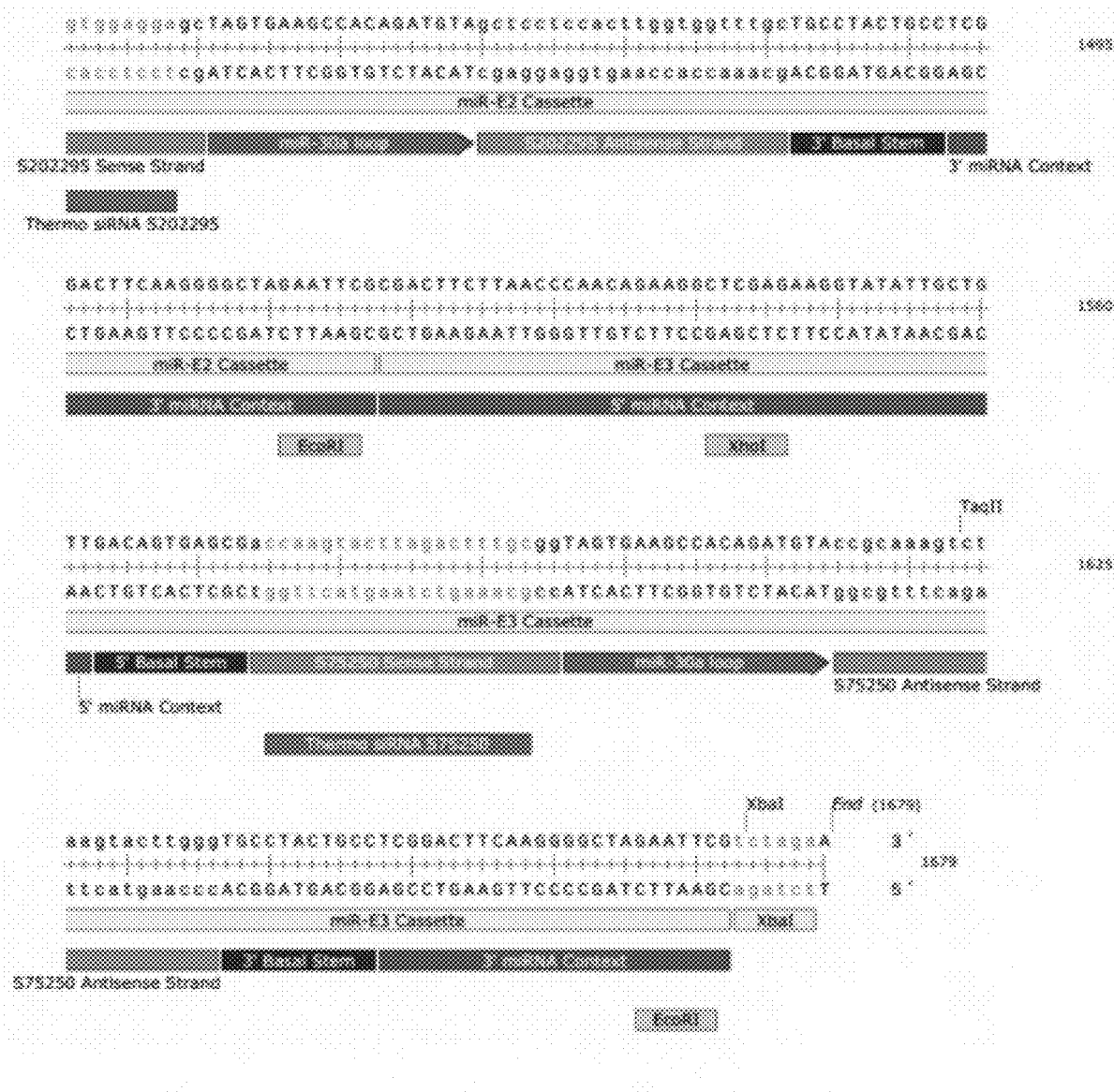
FIG. 5 is a schematic that represents a fifth portion of a plasmid vector of SEQ ID 7, according to embodiments of the present disclosure, which is contiguous with the fourth portion of FIG. 4.

Expression cassettes for expressing a monoclonal antibody (mAb) and/or a protein and/or interfering RNA were synthesized by Genscript. Each cassette contained a signal peptide, the variable heavy domain, the human IgG1 constant domain, the protein or the interfering RNA sequence followed by (when it is an Ab), a self-cleaving 2A peptide sequence, a signal peptide, the variable light domain and the human lambda constant domain. The synthesized mAb and/or protein and/or interfering RNA expression cassettes were cloned into the pAVA-00200 plasmid backbone containing the CASI promoter1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mAb and/or protein and/or interfering RNA expression cassette was amplified by PCR using Taq polymerase and the PCR products were gel purified and the bands on interest were also excised and purified using a gel extraction kit. These PCR products contained the mAb and/or protein and/or interfering RNA expression cassettes in addition to 15 base pair 5' and 3' overhangs that align with the ends of the linearized pAVA-00200 backbone. Using in-fusion cloning2, the amplified mAb or protein or interfering RNA expression cassettes are integrated with the pAVA-00200 backbone via homologous recombination. The resulting plasmid vectors contained the following 5' ITR, CASI promoter, monoclonal antibody or protein or interfering RNA expression cassette, WPRE, SV40 polyA and ITR 3', per SEQ ID 7 and as shown in five contiguous portions in FIG. 1, FIG. 2, FIG. 3, FIG. 4 and FIG. 5.

Example 2—Animal Studies

C57BL/6 mice and BALB/c mice were purchased from Charles River. AAV vectors of Example 1 were administered to 6-week-old C57BL/6 mice with the exception of the AAV vector that encoded mAb expression, which was tested in BALB/c mice. All animal experiments were approved by the institutional animal care committees of the Canadian Science Centre for Human and Animal Health and the University of Guelph. Intramuscular or intraorgan administration of the AAV were performed using a 29-gauge needle and a 40-µL injection volume. Injection into the tail vein was performed on mice that were warmed slightly, using a 100-µL injection volume. Intranasal administration of the AAV vectors were performed using a 40-µL injection volume. The dose used was about $2 \times 10^{11}$ vector genomes per mouse.

Example 3—Experimental Data

Table 2 below summarizes the data obtained from mice that received a hind flank, intramuscular administration of an AAV vector that encoded the belatacept similar protein (BSP) and three sequences of interfering RNA that target production of TNF-alpha. These mice were compared against a control. The data below came from a muscle biopsy sample taken from the hind flank region on the same side where the mouse received the intramuscular injection.

TABLE 2

BSP and TNF-alpha.

| Molecule | Control (ag) | AAV recipient (ag) | P-value |
|---|---|---|---|
| BSP | 0 | 9 | 0.0061 |
| TNF-alpha | 12 | 2 | 0.0151 | n.b. ag = attogram $1 \times 10^{-18}$ grams

As shown in Table 2, mice that received the AAV that included sequences that encoded for increased production of BSP demonstrated statistically significant higher amounts of BSP than the control mice that did not receive the AAV. Furthermore, mice that received the same AAV that encoded for increased production of three interfering RNA sequences also demonstrated a lower amount of TNF-alpha than the control mice. Without being bound by any particular theory, the mice who received the AAV had higher levels of BSP and lower TNF-alpha levels than mice that did not receive the AAV.

The invention claimed is:

1. A recombinant virus vector (RVV), the RVV comprising:

a) a nucleotide sequence encoding a belatacept-similar protein (BSP), wherein the nucleotide sequence encoding the BSP is SEQ ID NO: 1;

b) one or more nucleotide sequences encoding an interfering ribonucleic acid (RNA) that targets messenger ribonucleic acid (mRNA) of tumor necrosis alpha (TNF-alpha); and c) an inverted terminal repeat.

2. The RVV of claim 1, wherein the one or more nucleotide sequences encoding the interfering RNA are one or more of SEQ ID NO: 2, SEQ ID NO: 3 or SEQ ID NO: 4.

3. The RVV of claim 1, wherein the inverted terminal repeat is SEQ ID NO: 10.

4. The RVV of claim 3, wherein SEQ ID NO: 10 is adjacent a start region of the RVV, an end region of the RVV or both.

5. The RVV of claim 1, wherein the RVV comprises SEQ ID NO: 2, SEQ ID NO: 3 and SEQ ID NO: 4.

6. The RVV of claim 1, further comprising a first sequence of nucleotides that is positioned between a start region of the RVV and the SEQ ID NO: 1, and the first sequence of nucleotides have 95-99% the same nucleotides as SEQ ID NO: 8.

7. The RVV of claim 6, wherein the one or more nucleotide sequences encoding the interfering RNA is SEQ ID NO: 2 and wherein the RVV of claim 6 further comprises a second sequence of nucleotides that is positioned between SEQ ID NO: 1 and SEQ ID NO: 2 and that have 95-99% the same nucleotides as SEQ ID NO: 9.

8. The RVV of claim 1, wherein the RVV is an adeno-associated virus.

9. A composition that comprises a nucleotide sequence that can be expressed in a target cell, wherein the nucleotide sequence is SEQ ID NO: 7.

10. An insert for use with a recombinant virus vector (RVV), wherein the insert has a nucleotide sequence that is SEQ ID NO: 6.

* * * * *